(12) United States Patent
Klundt et al.

(10) Patent No.: US 8,858,572 B2
(45) Date of Patent: Oct. 14, 2014

(54) ENDOSCOPIC STITCHING MACHINE

(75) Inventors: Kurt Klundt, Hirschhorn (DE); Philipp Moll, Aachen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 1775 days.

(21) Appl. No.: 11/576,307

(22) PCT Filed: Nov. 15, 2005

(86) PCT No.: PCT/EP2005/012224
§ 371 (c)(1),
(2), (4) Date: Mar. 29, 2007

(87) PCT Pub. No.: WO2006/053710
PCT Pub. Date: May 26, 2006

(65) Prior Publication Data
US 2008/0071296 A1  Mar. 20, 2008

(30) Foreign Application Priority Data
Nov. 18, 2004  (DE) .......................... 10 2004 056 204

(51) Int. Cl.
*A61B 17/04* (2006.01)
*A61B 17/00* (2006.01)
*A61B 19/00* (2006.01)

(52) U.S. Cl.
CPC ......... *A61B 17/0491* (2013.01); *A61B 17/0469* (2013.01); *A61B 2017/0046* (2013.01); *A61B 2019/4868* (2013.01)
USPC ............................ 606/144; 606/139; 606/145

(58) Field of Classification Search
USPC ................................ 606/139, 144
See application file for complete search history.

(56) References Cited

U.S. PATENT DOCUMENTS

| 2,790,437 | A | * | 4/1957 | Moore ........................ 600/564 |
| 5,336,229 | A | * | 8/1994 | Noda ............................ 606/144 |
| 5,496,334 | A | * | 3/1996 | Klundt et al. ................ 606/145 |
| 5,545,170 | A | * | 8/1996 | Hart .............................. 606/148 |
| 5,593,402 | A | | 1/1997 | Patrick |
| 5,782,748 | A | * | 7/1998 | Palmer et al. ................ 600/104 |
| 5,947,996 | A | | 9/1999 | Logeman |
| 6,066,146 | A | * | 5/2000 | Carroll et al. ................ 606/148 |
| 6,077,290 | A | * | 6/2000 | Marini .......................... 606/205 |
| 6,126,359 | A | | 10/2000 | Dittrich et al. |
| 7,354,443 | B2 | * | 4/2008 | Moll et al. .................... 606/144 |

FOREIGN PATENT DOCUMENTS

DE   101 16 171 A1   10/2002
GB       872 952        7/1961

* cited by examiner

*Primary Examiner* — Melanie Tyson
*Assistant Examiner* — Todd J Scherbel
(74) *Attorney, Agent, or Firm* — McGlew and Tuttle, P.C.

(57) ABSTRACT

An endoscopic stitching machine, including a housing for mounting the actuators for the stitch-forming tools (needle, gripper and pressure pad), and a housing shaft to house one or more devices for the transmission of the movements generated by the actuators to the stitch-forming tools, whereby the housing shaft (3) and the transmission devices (9, 12, 13) are divided into two shaft parts (14, 15) and lower and upper transmission devices (9a, 12a, 13a and 9b, 12b, 13b), in a plane perpendicular to the longitudinal direction thereof, detachably connected to each other by means of a corresponding coupling piece (26), whereby the coupling pieces (26) may be introduced into and positively housed within corresponding recesses (32, 33) of the lower and upper transmission means (9a, 12a, 13a and 9b, 12b, 13b), parallel to the section plane and running in the longitudinal direction of the transmission devices (9, 12, 13).

19 Claims, 3 Drawing Sheets

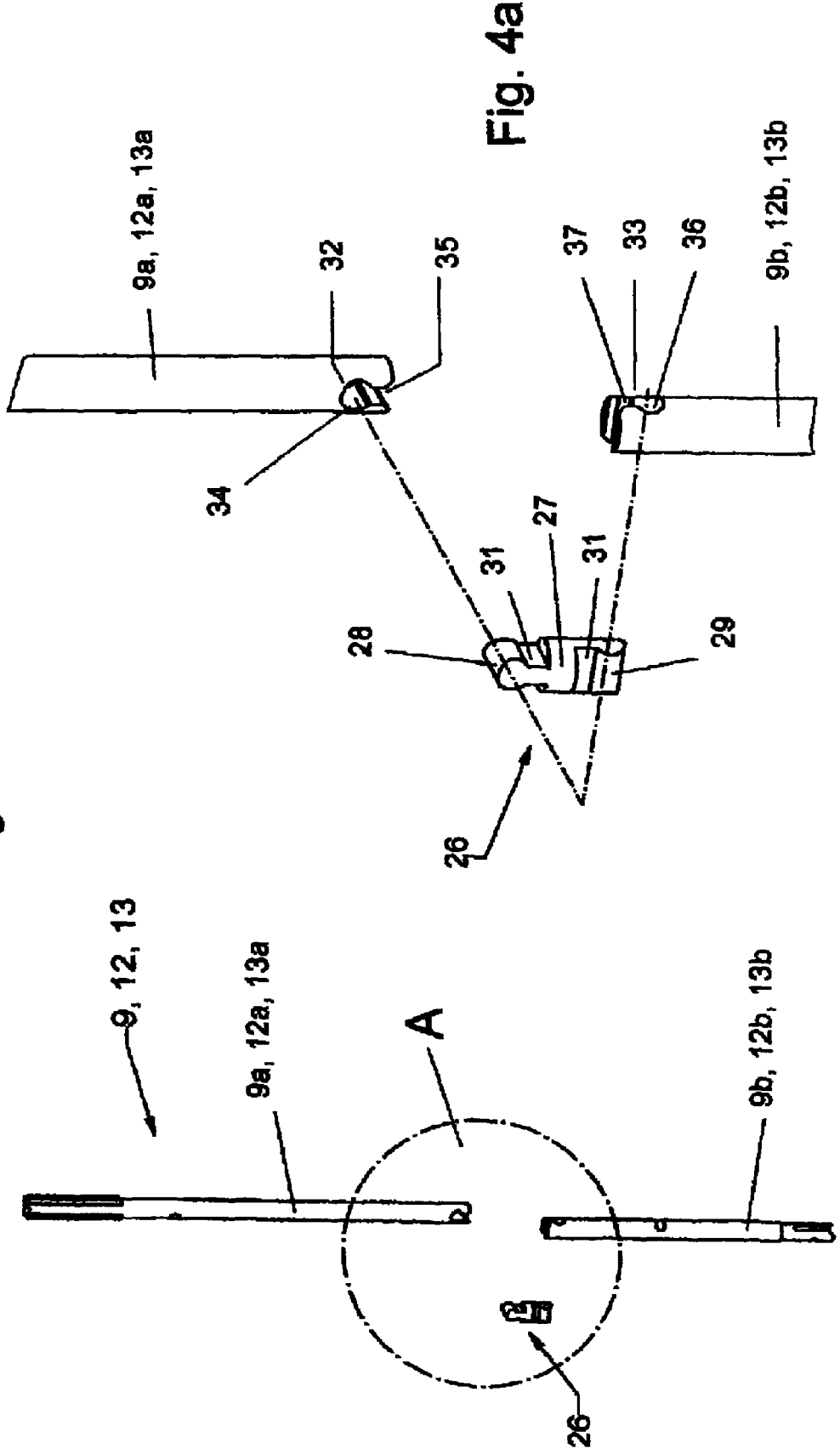

ENDOSCOPIC STITCHING MACHINE

Figure 1:
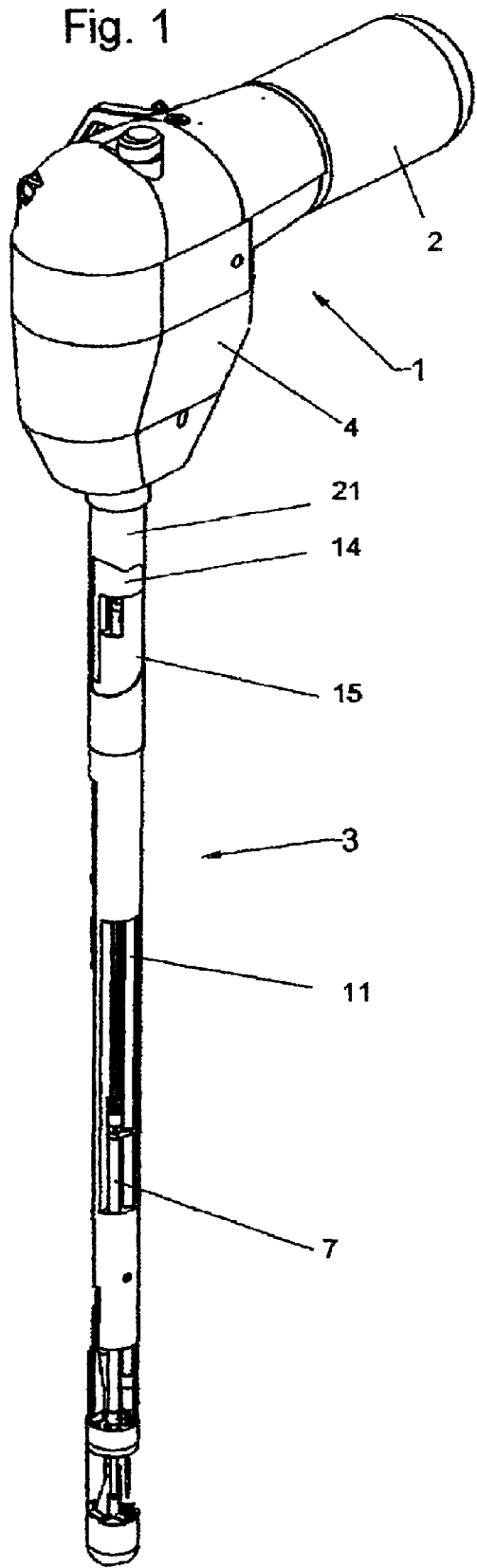

The invention relates to an endoscopic stitching machine according to the preamble of claim 1.

DE 101 16 171 A1 discloses a surgical suturing machine which is used in particular for making sutures inside the body of humans or animals. Since suturing machines of this type must be inserted at least partly into the human or animal body, it is desirable for the components to be inserted into the body to have the smallest possible volume. For this reason, not only the actual control elements but if possible also the drives for the stitch-forming tools such as needles, grippers and pressure pads, are located in a housing which remains outside the body. The movements produced by the various drives are therefore transmitted to the stitch-forming tools arranged at the end of the housing shaft by means of suitable transmission means accommodated by a housing shaft.

The resulting large overall length of the housing shaft and also the housing accommodating the various drives therefore make it very difficult to sterilize the parts of the surgical suturing machine coming in contact with the body, which is necessary after every intervention.

It is therefore the object of the invention to provide a solution which facilitates sterilization for a generic stitching machine whilst retaining the functional distance between the housing and the stitch-forming tools.

This object is achieved starting from a generic stitching machine whereby the housing shaft and the transmission means are divided within planes each running transversely to their longitudinal direction and the respective (lower and upper) sections of the transmission means are detachably connected to each other by means of respectively one coupling piece, whereby the coupling pieces can be introduced into and positively housed within corresponding recesses of the transmission means parallel to the plane of intersection and running in the longitudinal direction of the transmission means.

The term "transmission means" in this case is to be understood as those parts of the surgical suturing machine which transmit movements generated indirectly or directly by the respective drive for the stitch-forming tools (such as, for example, needles, grippers, pressure pads) to said tools. If the functional distance between the stitch-forming tools and the housing is relatively short, these can be the needle rod, gripper shaft and the pressure rod for the pressure pad itself or additional transmission means which are provided between the needle rod, the gripper shaft and the pressure rod for the pressure pad on the one hand and the corresponding exits of the individual drives on the other hand.

In this way, a type of plug connection is provided between the respective lower and upper sections of the transmission means or the needle rods, gripper shaft and the push rod for the pressure pad which allows the connection between the two parts of the respective transmission means or the needle rod, the gripper shaft or the push rod for the pressure pad to be broken and remade without tools whilst ensuring that the overall length of the transmission means of the coupling pieces is always the same.

If the releasing and joining of the transmission means which transmits the working movement for the needle to said needle takes place in the upper dead point area of its movement path, this position of the transmission means can serve as a reference position for the releasing and joining of the other transmission means whereby, in particular when joining the transmission means, the relative position between the sections of the transmission means connected to the respective drive and the sections of the transmission means carrying the stitch-forming tools is predefined and ensures that the respective sections of the transmission means are joined in the correct position without the assistance of auxiliary means.

A constructively favourable design of the coupling pieces suitable for the transmission of longitudinal and rotary movements of the transmission means is achieved if these have a central section at the front ends whereof, there is provided respectively one shaped part directed transversely to the longitudinal direction of the transmission means, which can be inserted into a recess of the transmission means corresponding to its cross-sectional shape.

In order to eliminate at center offset when joining the transmission means and/or to be able to compensate for a center offset co-used by manufacturing inaccuracies, the longitudinal axes of the two shaped parts of each coupling piece enclose an angle of 90 degrees.

In this case, it is furthermore advantageous if the shaped parts each have a prismatic and an adjoining substantially cylindrical region and the recesses of the transmission means are configured as complementary hereto.

In order to secure the two halves of the housing shaft longitudinally and transversely, its separation to form mutual bearing surfaces is step-shaped and in the separating region of one shaft part positioning means are provided for the other shaft part, which project into openings provided on the separating region of the other shaft part. In this case, the positioning means can be formed by dowel pins which engage in corresponding holes of the other shaft part. This facilitates the joining of the two shaft parts on the one hand and on the other hand, the positioning means together with the holes at the same time form a longitudinal securing of the two shaft parts.

In order to secure the position of the two shaft parts and also the relative position of the coupling pieces to the sections of the transmission means in the radial direction, the housing shaft is enclosed by a centering tube which is arranged concentrically to said shaft, which can be detachably connected to the upper shaft part by means of a locking device in the area of its end on the housing side.

In this case, it is advantageous if the locking device has a spring-loaded locking bolt which can be moved radially in the housing shaft which engages in a recess formed at the end of the centring tube on the housing side.

In order to facilitate the location of the correct relative position of the same when joining the sections of the transmission means and also to secure said position, in the circumferential area of the lower shaft part, two holes directed transversely to said part and parallel to one another are provided to receive a positioning aid, which holes simultaneously engage in cut-outs of the transmission means.

Further advantages and details of the invention are obtained with reference to the following description of an exemplary embodiment of the same which is shown in the appended drawing.

Figure 1B:
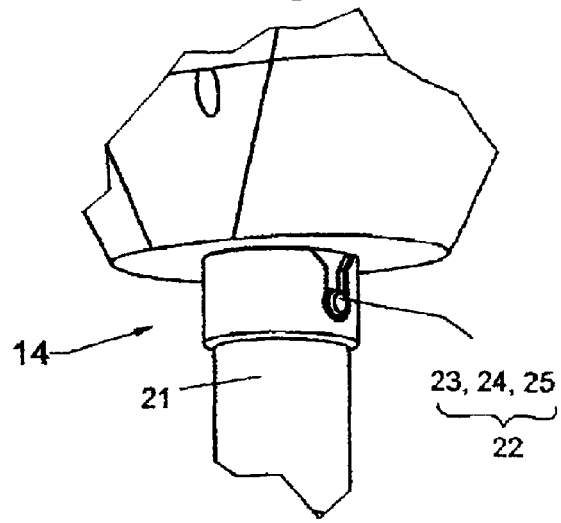
Figure 1A:
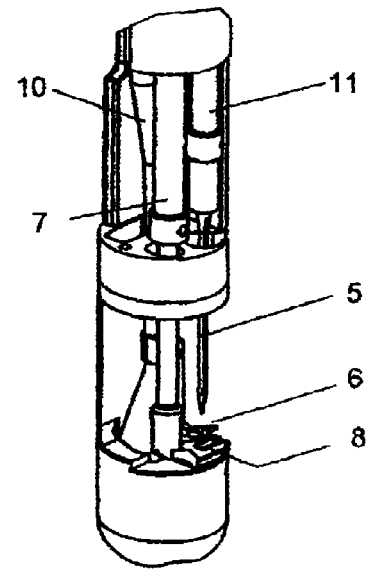
Figure 2:
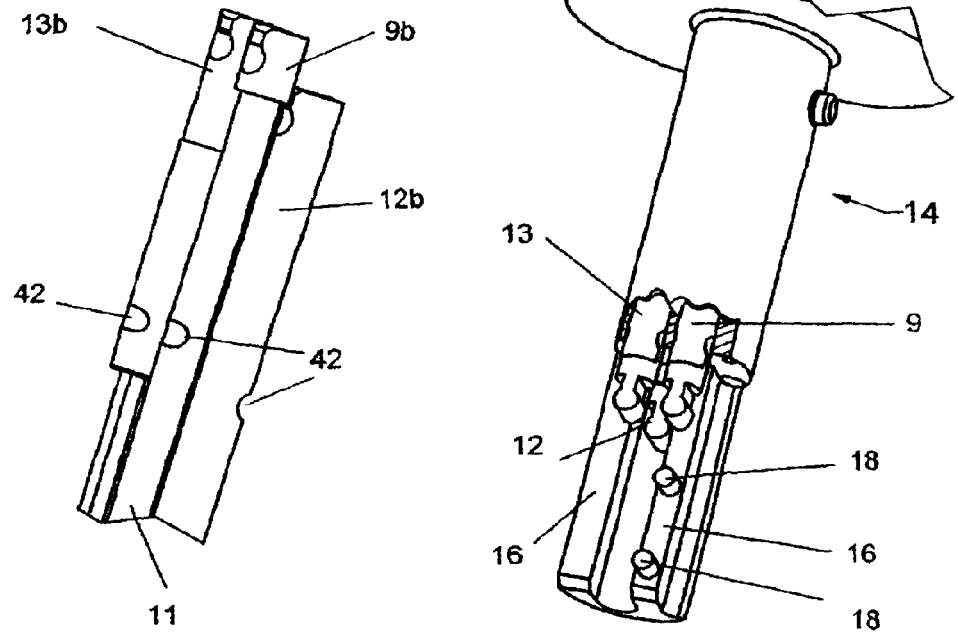
Figure 3:
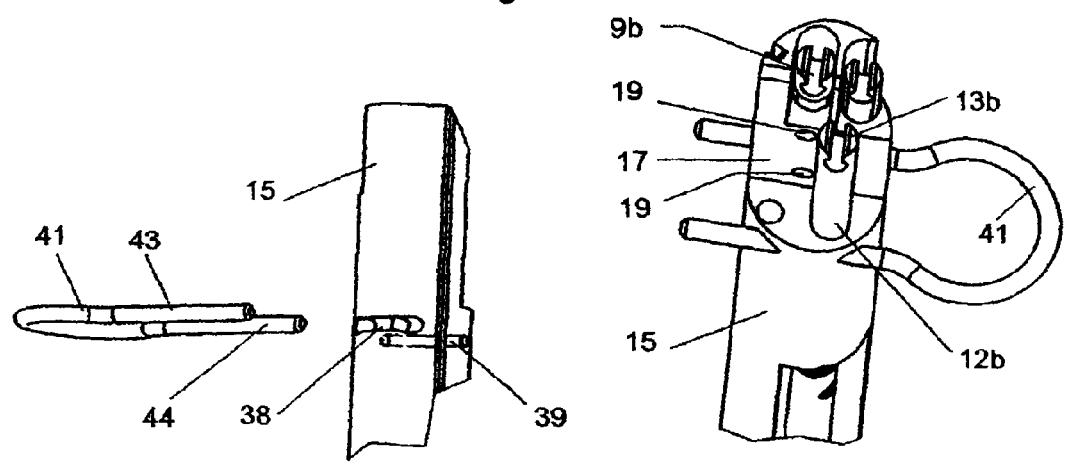

In the figures:

FIG. 1: is a schematic overall view of an endoscopic stitching machine;

FIG. 1a: is an enlarged view of the lower region of the shaft which holds the stitch-forming tools;

FIG. 1b: is an enlarged view of the upper shaft region with the centring tube;

FIG. 2: is an illustrative diagram of the upper shaft part together with the upper and lower transmission means;

FIG. 3: is an illustrative diagram of the lower shaft part with the lower transmission means and the positioning aid;

FIG. 4: is a detailed view of a transmission means with a coupling piece;

FIG. 4a: is an enlarged view of the detail "A" in FIG. 4;

The endoscopic stitching machine shown schematically in FIG. 1 has the same basic structure as the suturing machine described in DE 101 16 171 A1. Accordingly, the stitching machine according to the invention has a substantially L-shaped housing 1 which is formed by a gripping portion 2 embodied as a hollow body, a housing shaft 3 directed substantially perpendicular thereto and central housing portion 4 which joins said shaft to the gripping portion 2. Located inside the gripping portion 2 is an electric motor which is not shown, which is preferably embodied as a DC motor. The drive shaft, not shown, of the DC motor drives a main shaft via a clutch and a reducing gear, from which the movements for a needle 5 and a gripper 6 as well as for a pressure pad 8 are derived. The formation of the gearing used for this purpose is described in detail in the aforesaid DE 101 16 171 A1 so that its description is to be regarded as a component of the description of the present invention insofar as this is of interest for the understanding of the present invention.

Accordingly, the gearing has a needle drive which is drivingly connected via a transmission means 9 to the needle rod 11 carrying the needle 5 and imparts an upward and downward movement to the needle 5.

The gearing further has a swinging drive for the gripper 8 which executes a lifting movement and a swinging movement. The swinging drive is kinematically connected to the gripper shaft 10 via a transmission means 12 and imparts to said shaft both a lifting movement and a swinging movement. This transmission means 12 thus executes a lifting/swinging movement composed of a lifting and a swinging component and thus transmits both an alternating torque and also tensile and compressive forces.

Finally, a lifting movement of the pressure pad 8 is derived from the needle drive during the pushed-out phase of the needle 5 so that at least during a part of the pushed-out phase of the needle 5 the pressure pad 8 can hereby be periodically lifted by a certain amount to facilitate the advancing movement of the stitching material. For this purpose, a transmission means 13 is drivingly connected to the corresponding (not shown) driven member of the needle drive, whose movements are transmitted to a push rod 7 which is rigidly connected to the pressure pad 8.

As can be seen from FIGS. 2 and 3, the tubular housing shaft 3 is divided into an upper shaft part 14 and a lower shaft part 15 by a dividing plane running substantially transversely to its longitudinal direction. The dividing plane which is advantageously provided as close as possible to the end of the housing shaft on the housing side, runs in a step shape in this case as that bearing surfaces 16, 17 are formed on both shaft parts 14, 15. Both a radial and an axial alignment are hereby predefined when joining the two shaft parts 14, 15. In the area of the bearing surfaces 16 of the upper shaft part 14, positioning means formed by dowel pins 18 are fixed thereon, said means projecting into holes 19 formed in the area of the bearing surfaces 17 in the lower shaft part 15 when the housing shaft 3 is joined. The two shaft parts 14, 15 are thus secured in position in their longitudinal and transverse direction. When joined, the two shaft parts 14, 15 are surrounded by a centring tube 21 whose upper end can be detachably connected to the upper shaft portion 14 of the housing shaft 3 by means of a locking device 22. The locking device 22 has a locking bolt 23 which is arranged so that it can be displaced radially in the upper shaft part 14 and is pressed outwards under the action of a spring (not shown), said bolt engaging, when the centring tube 21 is pushed onto the housing shaft 3, in a recess provided thereon. This recess is formed by a transverse hole 25 substantially corresponding to the diameter of the locking belt 23, which is slitted towards the end of the centring tube 21.

The transmission means 9, 12, 13 connected to their relevant drive and guided in the housing shaft 3 are divided in their region corresponding to the separating position of the housing shaft within a plane running transversely to their longitudinal direction, into respectively two sections, namely into the respectively upper sections 9a, 12a and 13a and the respectively lower sections 9b, 12b and 13b and are detachably connected to one another by means of respectively one coupling piece 26 (FIG. 4, 4a). All the coupling pieces 26 have a standard design and are therefore provided with the reference numeral 26. Each of the coupling pieces 26 has a central portion 27 whose cross-sectional shape corresponds to the cross-section of the respective transmission means 9, 12 and 13. In the exemplary embodiment of the invention shown in the drawing, all the transmission means 9, 12, 13 uniformly have a circular cross-section so that all the central portions 27 of the coupling pieces 26 are embodied as cylindrical, their diameter being somewhat smaller than that of the transmission means. In the area of its two front ends, each coupling piece 28 is provided with a total of two shaped parts 28, 29 which are configured as substantially cylindrical in the exemplary embodiment shown and which are connected to the central portion 27 by means of respectively one web 31. As can be seen in particular from FIG. 4a of the drawing, the two shaped parts 28, 29 of each coupling piece 26 enclose an angle of preferably 90 degrees so that any centre offset of the two sections of the transmission means can thus be compensated.

The sections of the transmission means to be joined together using the coupling pieces 26 have recesses 32, 33 at their ends to be joined to one another, the shape of these recesses corresponding to the shape of the shaped parts 28, 29 and the webs 31. Accordingly, in the respectively lower regions of the respectively upper sections 9a, 12a and 13a of the transmission means 9, 12 and 13, there is provided respectively one transverse hole 34 which opens into a slot 35 which is open towards the front of the respective transmission means, its width being adopted to the width of the web 31. The shape of the recesses 32 is therefore determined by the transverse hole 34 and the slit 35.

Similarly, in the respectively upper regions of the respectively lower sections 9b, 12b and 13b of the transmission means 9, 12 and 13, there is provided respectively one transverse hole 36 running at an angle of 90 degrees to the transverse hole 34 which opens into a slot 37 which is open towards the front of the respective transmission means, its width being adapted to the width of the web 31. The shape of the recesses 33 is therefore determined by the corresponding transverse hole 36 and the slit 37.

Thus, the coupling pieces 26 can be displaced radially in the recesses 32, 33 to compensate for production inaccuracies or a centre offset but are held positively in the axial direction as a result of the shaping of the recesses 32, 33 and the shaped parts 28, 29. Since the centring tube 21 is guided over the housing shaft at the upper and lower sections of the transmission means which are interconnected by the coupling pieces 26 and the joined lower and upper shaft part, and is connected to said shaft by means of the locking device 22, the coupling pieces 26 are also positively secured in the radial direction. This means that the housing shaft 3 and the parts located in its interior form a structural unit which is held together without screw connections and can be dismantled for sterilization purposes into its components and joined together again without the assistance of tools.

In a preferred embodiment of the invention, the two shaped parts 28, 29 can be moved within the respective recess 32, 33 with a slight sliding fit. This is particularly important for compensating for centre offset and/or unavoidable production tolerances.

Since after their first joining, the shaped parts 28 of the coupling pieces 26 pertaining to the respectively upper sections 9a, 12a and 13a of the transmission means always adopt this angular position even in the case of subsequent multiple separation and respective re-joining of the transmission means, the position of the shaped parts 29 of the coupling pieces 26 assigned to the respectively lower sections 9b, 12b and 13b of the transmission means is thus predefined.

This means that when joining the respectively lower sections 9b, 12b and 13b of the transmission means, their relative position to the upper sections 9a, 12a and 13a is predetermined, i.e. the lower sections 9b, 12b and 13b are to be brought into a position in which they can be slid over the shaped parts 29 whereby their cylindrical region dips into the respective transverse hole 36 and the webs 31 slide into the respective slot 37.

In order to facilitate the location and securing of the joining position of the lower transmission means 9b, 12b and 13b, two holes 38, 39 directed transversely to its longitudinal axis and parallel to one another are provided in the circumferential region of the lower shaft part 15, forming recesses which are open on one side and preferably have a semicircular cross-section in the lower shaft part 15. Corresponding cut-outs 42 are provided on the lower transmission means 9b, 12b and 13b, forming cylindrical openings with the recesses formed by the holes 38, 39 in the lower shaft part 15 in the joining position of the lower transmission means 9b, 12b and 13b. The position of the cut-outs 42 on the lower transmission means 9b, 12b and 13b on the one hand and the position of the holes 38, 39 in the lower shaft part 15 on the other hand is selected so that when the cut-outs 42 are aligned with the holes 38, 39, the respective lower shaped parts 29 and the webs 31 of the coupling pieces 26 are directed parallel to the relevant hole 36 or to the corresponding slot 37 and can be inserted therein.

The respective cut-outs 42 and the holes 38, 39 are used to receive two legs 43, 44 of a positioning aid 41 which are located parallel to one another at a distance, whereby the joining position of the lower transmission means 9b, 12b and 13b is guided until the centring tube 21 slides over the area of the separating position of the shaft.

The invention claimed is:

1. An endoscopic stitching machine comprising:
a housing for mounting drives for stitch-forming tools, said stitch-forming tools comprising needles, a gripper and pressure pads;
a plurality of transmitting means for transmitting movements generated by the drives to said stitch-forming tools, said plurality of transmitting means comprising at least one thread-carrying needle and at least one gripper, said at least one gripper cooperating with said at least one thread-carrying needle, said at least one needle being movable in an upward and downward direction, said at least one gripper being mounted for movement such that said at least one gripper executes at least one oscillating movement per stitch-forming cycle; and
an adjoining housing shaft accommodating said transmitting means, said housing being connected to said housing shaft and each of said transmitting means being divided within a plane, said plane extending perpendicular to a longitudinal direction of said housing shaft and a longitudinal direction of each of said transmitting means, wherein said housing shaft is divided into an upper shaft part and a lower shaft part and each of said transmitting means is divided into a lower transmission means and an upper transmitting means, each of said lower transmitting means being detachably connected to one of said upper transmitting means via a coupling piece, each of said lower transmitting means and each of said upper transmitting means having a recess, wherein a portion of said coupling piece is arranged in each said recess, wherein said coupling piece is positively locked with said upper transmitting means and said lower transmitting means in said longitudinal direction, wherein each said portion of said coupling piece is movable within said recess in a direction parallel to said plane, each said coupling piece having two shaped parts extending transversely to the longitudinal direction of at least one of said transmitting means, one of said shaped parts being inserted into said recess of said upper transmitting means, another one of said shaped parts being inserted into said recess of said lower transmitting means, each said recess having a shape corresponding to a shape of one of said shaped parts, said two shaped parts, said recess of said upper transmitting means and said recess of said lower transmitting means being arranged within a circular cross-sectional area of one of said transmitting means.

2. An endoscopic stitching machine according to claim 1, wherein a longitudinal axis of one of said shaped parts of each coupling piece is perpendicular to a longitudinal axis of another one of said shaped parts.

3. An endoscopic stitching machine according to claim 1, wherein each of said shaped parts has a prismatic region and an adjoining substantially cylindrical region, said recess of said upper transmitting means having a prismatic shaped region, said recess of said lower transmitting means having a prismatic shaped region.

4. An endoscopic stitching machine according to claim 1, wherein each of said upper transmitting means is located at a spaced location from an end portion of said upper shaft part in a separation area of said housing shaft, each of said lower transmitting means being located at a spaced location from an end portion of said lower shaft part in said separation area of said housing shaft, said upper shaft part and said lower shaft part having bearing surfaces, one of said upper shaft part and said lower shaft part having a positioning means in said separation region of said housing shaft, another one of said upper shaft part and said lower shaft part having openings provided in said separation area of said housing shaft, said positioning means projecting into said openings.

5. An endoscopic stitching machine according to claim 1, wherein said housing shaft is enclosed by a centering tube which is arranged concentrically to said shaft.

6. An endoscopic stitching machine according to claim 5, wherein said centering tube has a housing side end, said centering tube being detachably connected to the housing shaft by means of a locking device on said housing side end.

7. An endoscopic stitching machine according to claim 6, wherein said locking device has a spring-loaded locking bolt which can be moved radially in the housing shaft which engages in a recess formed at the end of the centering tube on the housing side.

8. An endoscopic stitching machine according to claim 1, wherein a circumferential area of the lower shaft part, two holes directed transversely to said part and parallel to one another are provided to receive a positioning aid, which holes simultaneously engage in cut-outs of the transmission means.

9. An endoscopic stitching machine in accordance with claim 1, wherein each said recess extends in direction parallel to said plane, at least a portion of said coupling piece extending in a direction of said longitudinal direction of at least one of said transmitting means.

10. An endoscopic stitching machine comprising:
a plurality of stitch-forming tools comprising one or more needles, a gripper and pressure pads;
a plurality of drives for said stitch-forming tools;
a housing, said stitch-forming tools being mounted in said housing;
a first upper transmission means having a first upper transmission means end portion, said first upper transmission means end portion defining a first upper transmission means recess;
a second upper transmission means having a second upper transmission means end portion, said second upper transmission means end portion defining a second upper transmission means recess;
a first lower transmission means having a first lower transmission means end portion, said first lower transmission means end portion defining a first lower transmission means recess;
a second lower transmission means having a second lower transmission means end portion, said second lower transmission means end portion defining a second lower transmission means recess;
a first coupling piece;
a second coupling piece, said first upper transmission means being detachably connected to said first lower transmission means via said first coupling piece to form a first transmission means, wherein said first coupling piece is movable in a lateral direction with respect to said first lower transmission means and said first upper transmission means, said second upper transmission means being detachably connected to said second lower transmission means via said second coupling piece to form a second transmission means, wherein said second coupling piece is movable in a lateral direction with respect to said second lower transmission means and said second upper transmission means, said first upper transmission means recess receiving a portion of said first coupling piece, said first lower transmission means recess receiving another portion of said first coupling piece, said second upper transmission recess receiving a portion of said second coupling piece, said second lower transmission means recess receiving another portion of said second coupling piece, said first transmission means and said second transmission means for transmitting movements generated by the drives to said stitch-forming tools, said first transmission means comprising at least one thread-carrying needle, said second transmission means comprising at least one gripper, said at least one needle being movable in a linear direction, said at least one gripper being mounted for movement such that said at least one gripper moves in a radial direction;
an upper housing shaft part; and
a lower housing shaft part, said upper housing shaft part being detachably connected to said lower housing shaft part to form a housing shaft, said gripper and said thread-carrying needle being arranged in said housing shaft, said housing being connected to said housing shaft, wherein each of said first coupling piece and said second coupling piece has two shaped parts, said two shaped parts of said first coupling piece extending transversely to a longitudinal direction of said first transmission means, said two shaped parts of said second coupling piece extending transversely to a longitudinal direction of said second transmission means, one of said shaped parts of said first coupling piece being inserted into said first upper transmission means recess, another one of said shaped parts of said first coupling piece being inserted into said first lower transmission means recess, one of said shaped parts of said second coupling piece being inserted into said second upper transmission means recess, another one of said shaped parts of said second coupling piece being inserted into said second lower transmission means recess, said first upper transmission means recess having a shape corresponding to a shape of one of said shaped parts of said first coupling piece, said first lower transmission means recess having a shape corresponding to a shape of another one of said shaped parts of said first coupling piece, said second upper transmission means recess having a shape corresponding to a shape of one of said shaped parts of said second coupling piece, said second lower transmission means recess having a shape corresponding to a shape of another one of said shaped parts of said second coupling piece.

11. An endoscopic stitching machine according to claim 10, wherein a longitudinal axis of one of said shaped parts of said first coupling piece is perpendicular to a longitudinal axis of another one of said shaped parts of said first coupling piece, wherein a longitudinal axis of one of said shaped parts of said second coupling piece is perpendicular to a longitudinal axis of another one of said shaped parts of said second coupling piece.

12. An endoscopic stitching machine according to claim 11, wherein each of said shaped parts of said first coupling piece has a prismatic region and an adjoining substantially cylindrical region, said first upper transmission means recess having a prismatic shape region, said first lower transmission means recess having a prismatic shape region, each of said shaped parts of said second coupling piece having a prismatic region and an adjoining substantially cylindrical region, said second upper transmission means recess having a prismatic shape region, said second lower transmission means recess having a prismatic shape region.

13. An endoscopic stitching machine according to claim 10, wherein said first upper transmission means and said second upper transmission means is located at a spaced location from an end portion of said first upper shaft part in a separation area of said housing shaft, said first lower transmission means and said second lower transmission means being located at a spaced location from an end portion of said lower shaft part in said separation area of said housing shaft, said upper shaft part and said lower shaft part having bearing surfaces, one of said upper shaft part and said lower shaft part having a positioning means in said separation region of said housing shaft, another one of said upper shaft part and said lower shaft part having openings provided in said separation area of said housing shaft, said positioning means projecting into said openings.

14. An endoscopic stitching machine according to claim 10, wherein said housing shaft is enclosed by a centering tube which is arranged concentrically to said shaft.

15. An endoscopic stitching machine according to claim 14, wherein said centering tube has a housing side end, said centering tube being detachably connected to the housing shaft by means of a locking device on said housing side end.

16. An endoscopic stitching machine according to claim 15, wherein said locking device has a spring-loaded locking bolt which can be moved radially in the housing shaft which engages in a recess formed at the end of the centering tube on the housing side.

17. An endoscopic stitching machine according to claim 10, wherein a circumferential area of the lower shaft part, two holes directed transversely to said part and parallel to one another are provided to receive a positioning aid, which holes simultaneously engage in cut-outs of the transmission means.

18. An endoscopic stitching machine comprising:
a plurality of stitch-forming tools comprising one or more needles, a gripper and pressure pads;
a plurality of drives for said stitch-forming tools;
a housing, said stitch-forming tools being mounted in said housing;
a first upper transmission means having a first upper transmission means end surface, said first upper transmission means end surface defining a first upper transmission means recess;
a second upper transmission means having a second upper transmission end surface, said second upper transmission means end surface defining a second upper transmission means recess;
a first lower transmission means having a first lower transmission means end surface, said first lower transmission means end surface defining a first lower transmission means recess;
a second lower transmission means having a second lower transmission means end surface, said second lower transmission means end surface defining a second lower transmission means recess;
a first universal connection piece having a first universal connection piece portion and a second universal connection piece portion;
a second universal connection piece having a first portion and a second portion, said first upper transmission means being detachably connected to said first lower transmission means via said first universal connection piece to form a first transmission means, said first universal connection piece being detachably connected to said first lower transmission means and said first upper transmission means, said second upper transmission means being detachably connected to said second lower transmission means via said second universal connection piece to form a second transmission means, said second universal connection piece being detachably connected to said second upper transmission means and said second lower transmission means, said first upper transmission means recess receiving said first universal connection piece portion and said first lower transmission means recess receiving said second universal connection piece portion such that said first upper transmission means and said first lower transmission means are movable in a lateral direction with respect to each other via said first universal connection piece, wherein at least a portion of said first universal connection piece portion is in contact with at least a portion of said first upper transmission means end surface and at least a portion of said second universal connection piece portion is in contact with at least a portion of said first lower transmission means end surface, said second upper transmission recess receiving said first portion of said second universal connection piece and said second lower transmission means recess receiving said second portion of said second universal connection piece such that said second lower transmission means and said second upper transmission means are movable in a lateral direction with respect to each other via said second universal connection piece, wherein at least a portion of said first portion of said second universal connection piece is in contact with at least a portion of said second upper transmission end surface and at least a portion of said second portion of said second universal connection piece is in contact with at least a portion of said second lower transmission means end surface, said first transmission means and said second transmission means for transmitting movements generated by the drives to said stitch-forming tools, said first transmission means comprising at least one thread-carrying needle, said second transmission means comprising at least one gripper, said at least one needle being movable in a linear direction, said at least one gripper being mounted for movement such that said at least one gripper moves in a radial direction, said first and second universal connection piece portions of each of the first and second universal connection pieces extending transversely to a longitudinal direction of the first and second transmission means, respectively;
an upper housing shaft part; and
a lower housing shaft part, said upper housing shaft part being detachably connected to said lower housing shaft part to form a housing shaft, said gripper and said thread-carrying needle being arranged in said housing shaft, said housing being connected to said housing shaft.

19. An endoscopic stitching machine according to claim 18, wherein a longitudinal axis of said first universal connection piece portion of said first universal connection piece is perpendicular to a longitudinal axis of said second universal connection piece portion of said first coupling piece, wherein a longitudinal axis of said first portion of said second universal connection piece is perpendicular to a longitudinal axis of said second portion of said second universal connection piece.

* * * * *